United States Patent
Carstensen et al.

(10) Patent No.: US 11,730,917 B2
(45) Date of Patent: Aug. 22, 2023

(54) GAMMA STIMULATION PULSING LIGHT SOURCE SYSTEM WITH DOSAGE ADJUSTMENT FOR GAZE ANGLE

(71) Applicants: Optoceutics ApS, Kongens Lyngby (DK); Technical University of Denmark, Kgs. Lyngby (DK)

(72) Inventors: Marcus Carstensen, Frederiksberg (DK); Paul Michael Petersen, Hillerod (DK); Jes Broeng, Birkerod (DK); Mark Henney, Copenhagen (DK); Ngoc Mai Nguyen, San Jose, CA (US); Robert Dobkin, Monte Sereno, CA (US)

(73) Assignee: Optoceutics ApS, Copenhagen (DK)

( * ) Notice: Subject to any disclaimer, the term of this patent is extended or adjusted under 35 U.S.C. 154(b) by 279 days.

(21) Appl. No.: 17/084,275

(22) Filed: Oct. 29, 2020

(65) Prior Publication Data
US 2022/0134047 A1  May 5, 2022

(51) Int. Cl.
*A61M 21/02* (2006.01)
*G16H 20/40* (2018.01)
(Continued)

(52) U.S. Cl.
CPC ........... *A61M 21/02* (2013.01); *G16H 20/40* (2018.01); *G16H 20/70* (2018.01); *G16H 40/67* (2018.01);
(Continued)

(58) Field of Classification Search
CPC .......... A61M 21/02; A61M 2021/0044; A61M 2205/3303; A61M 2205/583; G16H 20/40;
(Continued)

(56) References Cited

U.S. PATENT DOCUMENTS

| | | | |
|---|---|---|---|
| 5,149,317 A | * | 9/1992 | Robinson ............... A61M 21/00 600/27 |
| 10,159,816 B2 | | 12/2018 | Tsai et al. |

(Continued)

FOREIGN PATENT DOCUMENTS

WO    2018152255 A1    8/2018

OTHER PUBLICATIONS

PCTUS2021056478 Written Opinion.
(Continued)

*Primary Examiner* — Sunita Reddy
(74) *Attorney, Agent, or Firm* — Patent Law Group; Brian Ogonowsky

(57) ABSTRACT

Gamma brain stimulation for preventing or treating Alzheimer's disease or sleeping disorders using light or sound is known. A strobing 40 Hz light source has been shown to cause positive effects due to the stimulation. It is an advantage to know the actual dosage of light that enters the person's eyes in order to understand the relationship between dosage and effectiveness. A camera is used to detect the subject's gaze angle, distance, pupil diameter and any other factors that affect the light power that enters the eye. A target dosage is first determined by a medical worker, such as to determine the effects of the exact same dosage on a group of similar persons, such as Alzheimer's patients. With deviations of gaze angle, distance, and pupil size from the ideal, the effective dosage is decreased. The disclosed system adjusts the actual dosage, such as session duration, based on such factors so that the final dosage received by the person is consistent and meets the target dosage.

10 Claims, 4 Drawing Sheets

(51) Int. Cl.
*G16H 40/67* (2018.01)
*G16H 20/70* (2018.01)
*G16H 10/60* (2018.01)
*A61B 3/11* (2006.01)
*A61B 3/113* (2006.01)
*A61B 3/14* (2006.01)
*A61M 21/00* (2006.01)

(52) U.S. Cl.
CPC ............... *A61B 3/112* (2013.01); *A61B 3/113* (2013.01); *A61B 3/14* (2013.01); *A61M 2021/0044* (2013.01); *A61M 2205/3303* (2013.01); *A61M 2205/583* (2013.01); *G16H 10/60* (2018.01)

(58) Field of Classification Search
CPC ........ G16H 20/70; G16H 40/67; G16H 10/60; A61B 3/112; A61B 3/113; A61B 3/14; A61N 5/0618; A61N 2005/0648; A61N 5/0622
USPC ...................................................... 600/27–29
See application file for complete search history.

(56) References Cited

U.S. PATENT DOCUMENTS

| | | | |
|---|---|---|---|
| 2010/0016841 A1* | 1/2010 | De Taboada | A61N 5/0622 606/2 |
| 2010/0121158 A1* | 5/2010 | Quevedo | A61B 5/411 600/301 |
| 2018/0333590 A1* | 11/2018 | Millard | A61N 5/0618 |
| 2019/0255350 A1 | 8/2019 | Malchano | |
| 2019/0290882 A1* | 9/2019 | Chao | A61B 5/11 |
| 2019/0335551 A1* | 10/2019 | Williams | H05B 45/24 |
| 2020/0108270 A1* | 4/2020 | LaVine | G02F 1/137 |
| 2020/0269065 A1 | 8/2020 | Broeng et al. | |
| 2020/0360715 A1* | 11/2020 | Lim | A61N 5/0622 |
| 2020/0398021 A1* | 12/2020 | Garza | A61N 2/006 |

OTHER PUBLICATIONS

Carstensen et al., "40 Hz Invisible Spectral Flicker and Its Potential Use in Alzheimer's Light Therapy Treatment," Proceedings of SPIE, SPIE BiOS, 2020, San Francisco, CA, USA.

* cited by examiner

's gaze angle or other changing viewing characteristics. The invention also applies to other optical pulse frequencies, such as beta brain stimulation for sleep disorders.

GAMMA STIMULATION PULSING LIGHT SOURCE SYSTEM WITH DOSAGE ADJUSTMENT FOR GAZE ANGLE

FIELD OF THE INVENTION

The invention primarily relates to optical (or photonic) gamma brain stimulation for treating or preventing certain diseases, such as Alzheimer's disease, dementia, or circadian rhythm sleep disorders, and, more particularly, to a light dosage adjustment system that provides a target effective dosage of the gamma brain stimulation irrespective of a subject's gaze angle or other changing viewing characteristics. The invention also applies to other optical pulse frequencies, such as beta brain stimulation for sleep disorders.

BACKGROUND

Research has provided evidence in mice that stimulation of gamma brain waves reduces Alzheimer's-related proteins and slows neurodegeneration associated with the disease. Gamma brain waves are electrical charges that help link and process information from all parts of the brain. It is believed that similar advantageous effects occur in humans, and such research is on-going.

Healthy brains feature rhythmic patterns, or brain waves, that operate at different frequencies. Gamma brain waves, which oscillate at roughly from 20 to 140 Hz, are associated with higher-order cognitive functions and are known to decrease in the brains of people with Alzheimer's disease and other neurological or psychiatric disorders.

It has been discovered that exposing Alzheimer's mouse models to visible-wavelength LED lights flickering (i.e., strobing) at 40 Hz stimulates gamma waves, which not only reduces levels of beta-amyloid and tau (proteins associated with Alzheimer's) but also boosts the activity of microglia in clearing harmful debris. In other words, such strobing triggers brain wave oscillations around 40 Hz.

Further details of the effects of optical gamma brain stimulation can be found in published applications WO2018/152255 and US 2020/0269065, both incorporated herein by reference. Many more publications describe such effects.

Gamma wave stimulation using sound (e.g., clicks played at 40 Hz) in Alzheimer's mouse models has related positive effects.

Using optical or sound gamma stimulation resulted in stimulated mice performing better on memory tasks, including recognizing objects and navigating a water maze to find a hidden platform. Researchers also saw changes in activation responses in microglia and astrocytes (cells involved in clearing debris) and in blood vessels.

Mice exposed to a combination of light and sound gamma stimulation expanded the effects beyond the visual and auditory cortex to the prefrontal cortex, an area of the brain important for planning and completing tasks. Using imaging analysis, the scientists found a unique clustering effect of microglia around amyloid deposits in stimulated mice and reduced amyloid pathology. The effects were short-lived, however, diminishing a week after stimulation.

In a study published in the periodical Neuron, MIT researchers tested the effects of longer-term treatment by exposing mouse models with more advanced Alzheimer's disease to up to 6 weeks of gamma entrainment by visual stimulation. Results showed stimulation increased gamma brain waves in the visual cortex and higher-order brain areas, including the hippocampus and prefrontal cortex. Continuing stimulation also preserved neuronal and synaptic density in these brain regions, improved performance on memory tasks, and reduced inflammation. Findings point to an overall neuroprotective effect, even in the later stages of neurodegeneration, the researchers reported.

Results of this research add to previous investigations of gamma wave stimulation as a possible treatment for Alzheimer's disease in humans.

Using a strip of LED lights that flickered at different speeds, the researchers found that a single, hour-long treatment of light flashing at 40 Hz increased gamma waves and reduced beta-amyloid levels by half in the visual cortex of mice in the very early stages of Alzheimer's. Within 24 hours, however, amyloid levels returned to normal in this brain region, which processes information from the eyes. When the scientists exposed mice with even higher levels of amyloid buildup to 1 hour of flickering light per day over 7 days, the number of amyloid plaques and levels of free-floating amyloid decreased. The treatment also ramped up the efficiency of microglia, reducing the number of amyloid plaques and free-floating amyloid.

As seen, repeated treatments are required for the gamma brain stimulation, which are very time-consuming for the person. Optimal dosages of the gamma brain stimulation light are being determined. The effective dosage of the flickering light depends on whether the person is looking directly at the light (maximum exposure) or looking away from the light (minimum exposure). An EEG (electroencephalography) may be used to detect progress in the treatment, but such a test is impractical in the person's home. So, accurately measuring the dosage is very important for tracking the treatment.

It is desirable for the person to conduct his/her own gamma brain stimulation in his/her own home at any time. It is also desirable for the gamma brain stimulation system to be entirely automated so the person's dosage is optimal. Therefore, what is needed is an automatic, optical gamma brain stimulation system that provides a pre-programmed optimal dosage to the person irrespective of the person's gaze angle, eye distance, or pupil size with respect to the light source.

SUMMARY

An optical (or photonic) gamma brain stimulation system is disclosed that flickers one or more light sources, such as white light or blue light LEDs, within the gamma range, such as at a rate of 40 Hz. A gamma brain stimulation rate range between 20 Hz-140 Hz may be effective. A duty cycle of 50% is sufficient, but the duty cycle is not critical. The light source output power should be at a comfortable level for the person, such as a patient or any other person looking at it, and a precise output power does not seem critical. The optimal dosage is preprogrammed into the system. An optimal dosage for the particular person, such as a patient, may be, for example, one continuous hour every day for example at 9 am. By precisely monitoring dosages for many similar persons and storing the information, while also testing the persons for changes in the disease, a correlation can then be developed between dosage and patient improvement.

Various areas of the brain can be stimulated by optical brain stimulation treatment such as the hippocampus, amygdala, prefrontal cortex (PFC), visual cortex (VC), and the suprachiasmatic nucleus (SCN). The ability to determine the optimal target effective dosage of optical brain stimulation for these particular areas of the brain will aid in the treatment of diseases that are associated with neurodegeneration. In particular, understanding the minimal dosage required to activate the hippocampus and SCN to affect circadian rhythm (often associated with early onset of Alzheimer's) may allow for individualize/personalize treatment of diseases.

One can examine dose dependence of activation of cytokines within 15 minutes of light exposure, while it takes 60 minutes to activate autoimmune cells. So, knowing when certain enzyme and transcription/translation activation occurs is important in determining the required treatment duration (or dosage), and the treatment can be personalized to each person.

To provide a more accurate determination of the effective dosage, an eye tracking system detects the person's gaze angle relative to the light source during the stimulation session. A maximum dosage is delivered when the person is directly looking at the light source at a particular distance (e.g., 50 cm). In that case, the dosage time can be the minimum. If the person looks away from the light source for periods of time during the treatment, the non-zero gaze angle is processed using an algorithm to extend the dosage time so the person receives the overall correct dosage for the day.

The gaze tracker can also determine the distance the eye is from the light source and the diameter of the pupil. These factors also affect the effective dosage, and the system dynamically controls the dosage time or even the light output power to compensate for eye distance and pupil size.

A display may tell the person the remaining time for the treatment, which dynamically adjusts for the person's gaze. Therefore, the person is encouraged to gaze directly at the light source to minimize the session time.

The system may be incorporated into a desk-supported system, portable screens and tablets, smart phones, flat or curved screens, wearable goggles, or other types of flat, curved, round or otherwise differently shaped optical screen or light-source systems.

BRIEF DESCRIPTION OF THE DRAWINGS

Elements labelled with the same numerals in the various drawings may be the same or equivalent.

DETAILED DESCRIPTION

Figure 1:
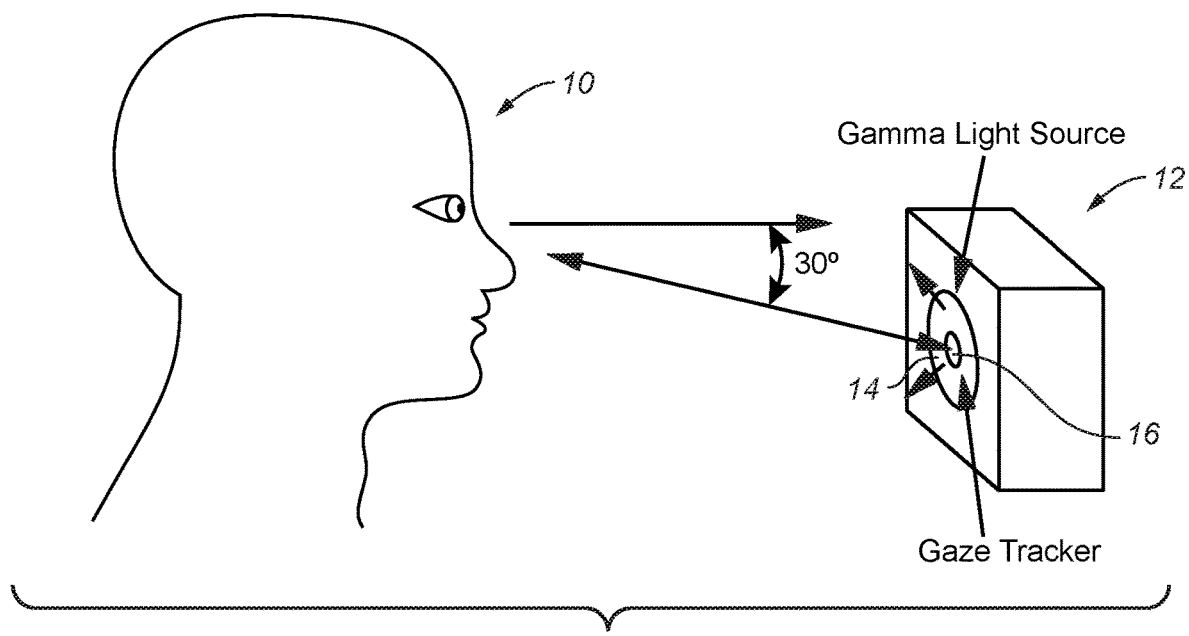
FIG. 1 illustrates the optical gamma brain stimulator with a dosage adjuster, in accordance with one embodiment of the invention.

FIG. 1 illustrates a subject, such as a person 10, that either has been diagnosed with Alzheimer's disease or may be at risk of developing Alzheimer's or a related disease, or diagnosed with a circadian rhythm sleeping disorder, that may be treated with optical gamma brain stimulation. The person 10 may additionally be subjected to or treated with sound gamma brain stimulation.

A gamma brain stimulation light system 12 is positioned about 50-100 cm from the person 10. The system may be supported by a table or desk. In another embodiment, the system forms goggles that are worn by the person 10.

In one embodiment, a pulsing light source 14 uses blue light LEDs, white light LEDs, or a variety of different wavelength monochromatic LEDs. The flickering is near to imperceptible at 40 Hz. The LEDs are optionally arranged to form a circular light source 14 with a camera lens 16 in the middle. In another embodiment, the light source 14 may be more of a point source, and the camera lens 16 may be next to it. In that case, the gaze angle is adjusted for the offset of the lens and the light source. The light source 14 may instead be a flat two-dimensional array of LEDs, such as 20 cm×20 cm diffused Lambertian source.

The overall dosage of light for the person 10 may be determined by a medical worker based on clinical trials and testing. Optimal dosage levels for different types of persons, such as patients, are still being studied, but a reasonable dosage is one-hour of the person 10 looking directly at the light source 14. Such a session may be performed at the same time every day. The person 10 may be periodically evaluated by a medical worker to correlate the gamma brain stimulation with the effects of Alzheimer's or other disorder. Cognitive testing may be done as well as testing to determine the presence of certain proteins and other chemicals in the person's body. Testing may include an EEG (electroencephalography). It is vital, for evaluation, to know exactly what dosage of light has been given to the person 10.

The Applicants have discovered that the effective dosage of neural entrainment light is highly influenced by combinations of gaze angle, eye distance from the light source, and pupil size, although compensation for any one of these factors helps achieve the target dosage. The actual dosage corresponds to a certain brain stimulation session duration given the particular gaze angles, eye distances, and pupil sizes during the session. Adjustments for gaze angle are the most significant for achieving the target light dosage.

The camera 18 (FIG. 2) and lens 16 may be of a conventional type used for gaze tracking. Conventional software and processing hardware may also be used to detect the gaze angle, eye/face distance, and pupil size. The camera 18 may emit infrared signals and detect the reflection in order to determine the gaze angle, eye/face distance, and pupil size. Alternatively, the camera 18 may use image processing to calculate gaze angle, eye/face distance, and pupil size. Calibration by the person may be initially used to establish baselines, where the person 10 is instructed to look at different areas at different distances to establish the baseline data. That baseline data is then stored in a memory for later comparison to the data collected during a session.

A target light dosage is first established by the medical worker for the person 10 and this information is downloaded into the system 12, such as through the Internet. The target light dosage correlates to the session duration, given a known light optical output power and pulse frequency, with the person at a particular distance from the light source with an average pupil size. In one example, this target dosage assumes the person 10 is directly looking at the light source 14 at a distance of 50 cm with an average pupil size. The actual effective dosage, however, is reduced if the person 10 does not look directly at the light source 14, or is further than 50 cm away, or has a smaller than average pupil size.

As described with respect to FIGS. 2-5, the gaze angle, eye distance from the light source, and pupil size are automatically detected by the camera and algorithms, and the session duration is expanded as necessary to achieve the predetermined target light dosage. For example, a gaze angle of 0° is looking directly at the light source 14, so the person 10 receives 100% of the dosage at 50 cm with average pupil size. A gaze angle of 90° results in the person 10 receiving 0% of the light, and a gaze angle of 45° results in the person 10 receiving 50% of the light. The correlation between detected gaze angle and light reception may be linearly extrapolated between 0-100%, or the correlation may be non-linear based on empirical results.

The detected distance from the light source will have a non-linear correlation to the actual effective dosage, since the effect of the light is non-linearly diminished as the person 10 moves from 50 cm to 100 cm from the light source. Similarly, the pupil size has a non-linear effect on the actual dosage.

Figure 2:
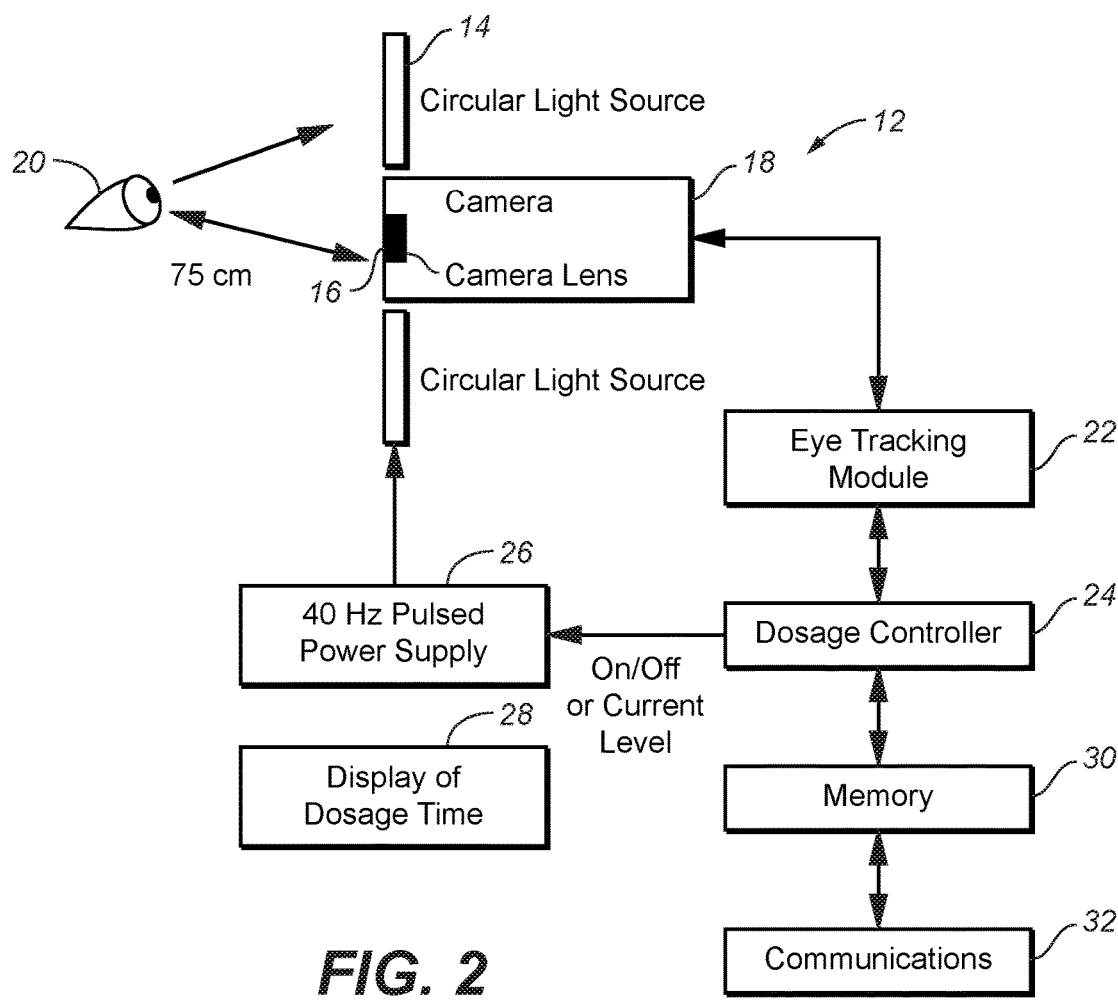
FIG. 2 illustrates various modules in the system.

In FIG. 2, the person's eye 20 is assumed to be looking above the light source 14. The camera 18, using image frames or reflected IR light, determines the gaze angle, distance, and pupil size. Gaze detection is commonly used in conjunction with display screens to detect which icon on the screen is being viewed by the viewer, and then to select that icon automatically. Gaze detection is also used in the retail industry to determine where a potential customer is looking. Gaze angle detection, including distance detection, is also used in various other fields and such systems are commercially available and inexpensive.

Suitable gaze detection systems for customization are available from SR Research, Tobii AB, and other companies. A fully customized system can also be fabricated using a Raspberry Pi Camera Module v2 in conjunction with a Raspberry Pi 3 Model B+ single board computer. Much of the software is commercially available.

The raw digital data from the camera 18 is then processed by a processor running an algorithm in the eye tracking module 22. Such algorithms may consist of publically available software customized for the present invention. For the present invention, the software uses the resulting information about gaze angle, distance, and pupil size to dynamically control the dosage so that the person 10 ultimately receives the target dosage, in particular when the person is a patient.

The output of the eye tracking module 22 is then used to adjust the dosage that is controlled by the dosage controller 24. The dosage controller 24 initially receives a target dosage from the medical worker, which may correlate to a one hour session. This target session time is then automatically extended based on deviations from the ideal conditions of direct gaze, 50 cm distance, and average pupil size.

FIG. 2 shows the dosage controller 24 controlling a 40 Hz current pulse power supply 26 to be on a certain amount of time. The dosage controller 24 may also control the current applied to the light source 14.

The required session time is displayed to the person 10 on a display screen 28, so the person 10 knows that the session time has been extended due to the person 10 gazing away or being further than 50 cm from the light source 14. The display screen 28 may use data generated by the local system or generated by a remote system communicating via the Internet.

A memory 30 stores the results of the session so the medical worker has accurate data regarding the dosage.

Communications hardware 32 may convey the data to the medical worker and update the system with upcoming session information.

Figure 3:
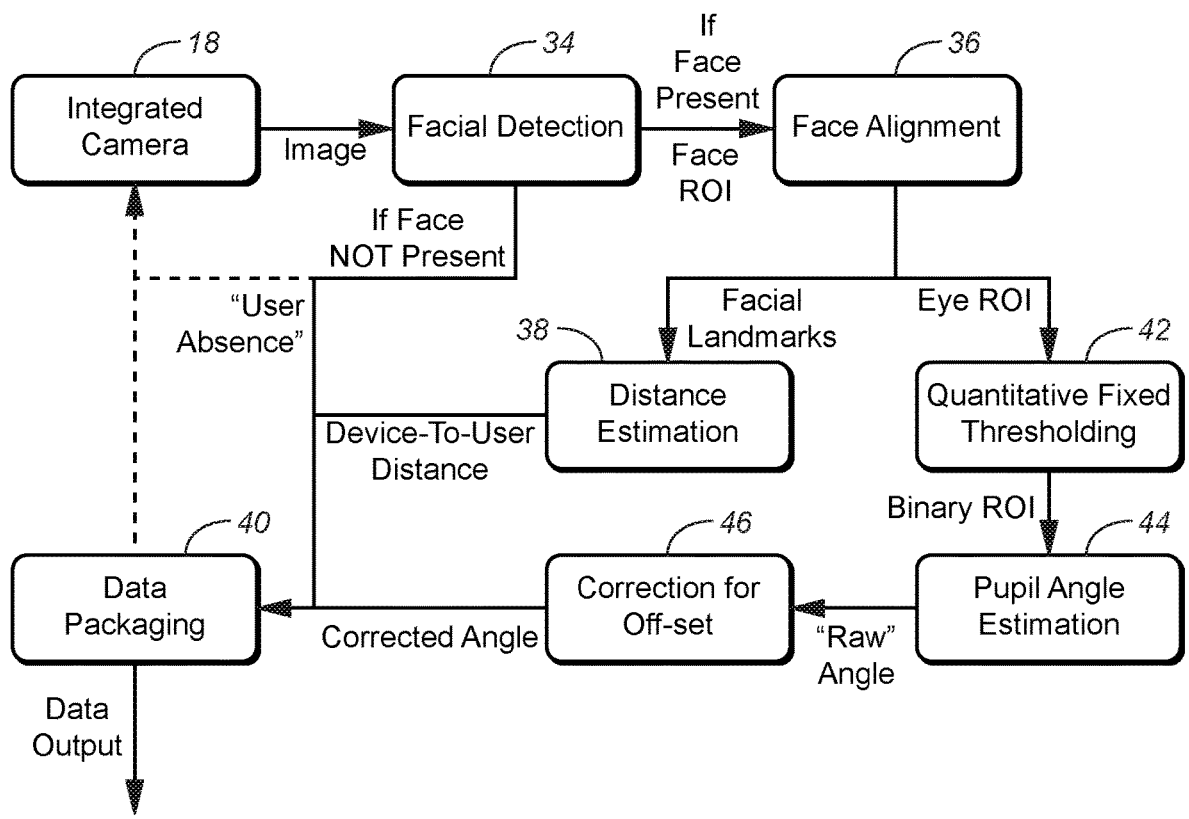
FIG. 3 illustrates the optical detection aspect of the system in more detail.

FIG. 3 illustrates more detail about one embodiment of a suitable camera and algorithms. The algorithms and processor would be within the eye tracking module 22 of FIG. 2. The camera 18 captures an image of the person's face and eye position and analyzes the image. In other systems, IR is reflected off the person and the reflected light is processed. It is assumed that the system has undergone an initial calibration by the person.

In FIG. 3, the face is detected (block 34), such as using a Viola-Jones object detection algorithm. The face is the region of interest (ROI). If a face is detected, the ROI information is passed to a facial alignment block 36 that detects relative distances between facial features for distance estimation (block 38). The calculated distance is then provided in a data package (block 40).

The eyes are also detected and processed by quantitative fixed thresholding algorithms (block 42). This process uses contrast thresholds (binarization) to determine objects, such as irises and pupils. Based on this data, the pupil angle is estimated (block 44). From this, the angle of gaze is computed trigonometrically and, after correcting for any off-set (block 46) of the integrated camera 18 lens relative to the light source, the resulting angle is passed to the data packaging block 40 before capturing the next frame. The dosage may be adjusted dynamically from frame to frame or may just be adjusted nearer the end of the session.

If no face is detected, a "user absence" signal is generated, and no power is applied to the light source.

The packaged data is applied to the dosage controller 24 of FIG. 2, as previously described, to adjust the session duration.

Figure 4:
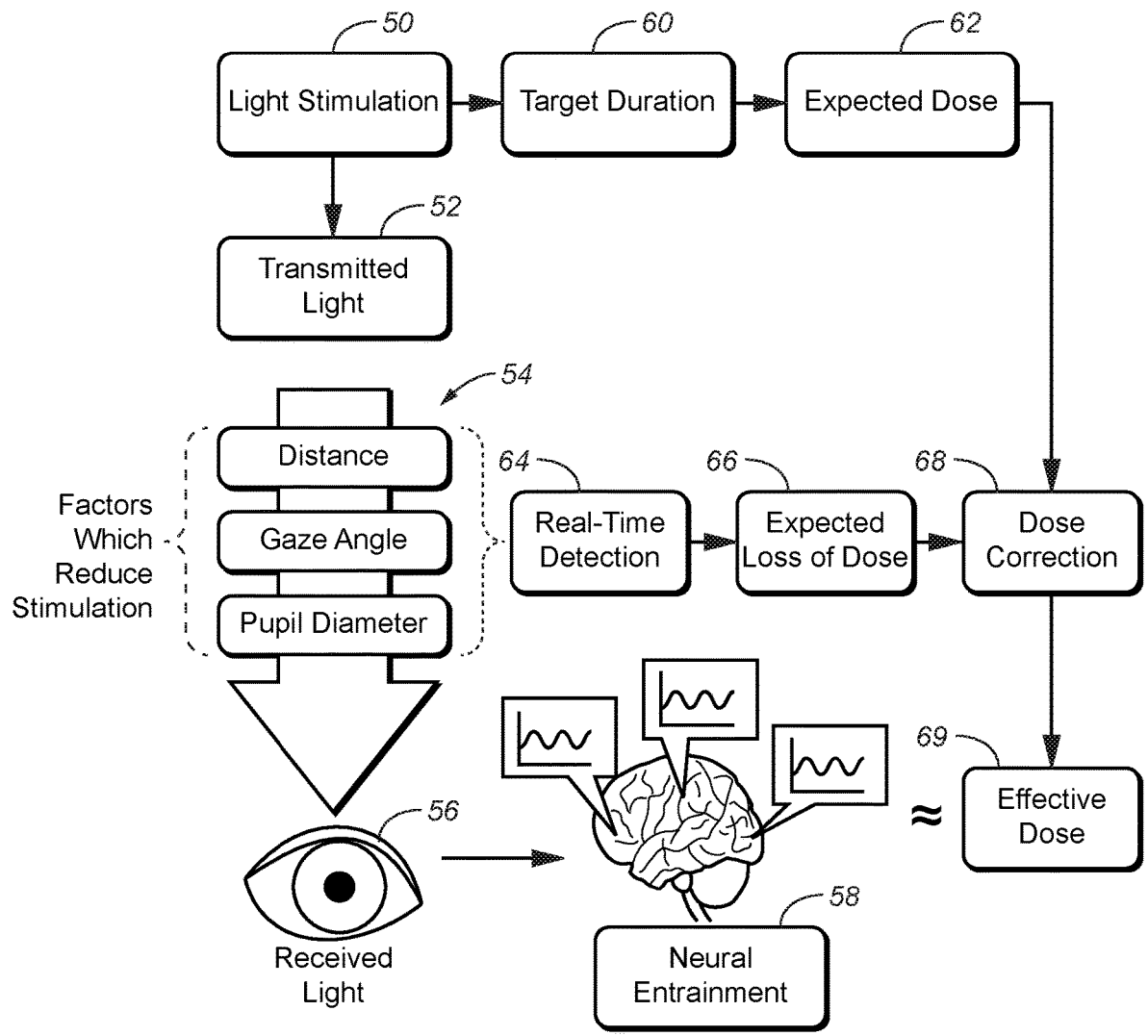
FIG. 4 is a flow chart illustrating the effect of various factors on gamma brain stimulation dosage.

FIG. 4 is a flowchart showing the steps for dynamically controlling the dosage.

In step 50, the 40 Hz strobing light source is turned on to emit the stimulating light 52. The gaze detection system detects the person's distance, gaze angle, and pupil diameter (step 54) as the person's eye receives the light (step 56). The brain then undergoes neural entrainment (step 58) (i.e., the capacity of the brain to naturally synchronize its brainwave frequencies with the rhythm of periodic external stimuli).

The target duration (step 60), provided by the medical worker or other source, is correlated with an expected or target dosage of the light (step 62). The real-time detection (step 64) during the analysis of step 54 is then correlated to any expected loss of dosage (step 66) due to gaze angle, etc. A look-up table may be used to correlate the data with the loss of dosage.

The dose correction step 68 then subtracts the loss of dose from the "ideal conditions" dose to derive the actual effective dose being received by the person. The effective dose information (step 69) is then used to extend the session, as needed, to achieve the target dose.

The data obtained from the session and from testing the person, such as in particular a patient, may be used to further the understanding of the effects of the gamma brain stimulation on, for example, Alzheimer's disease.

Figure 5:
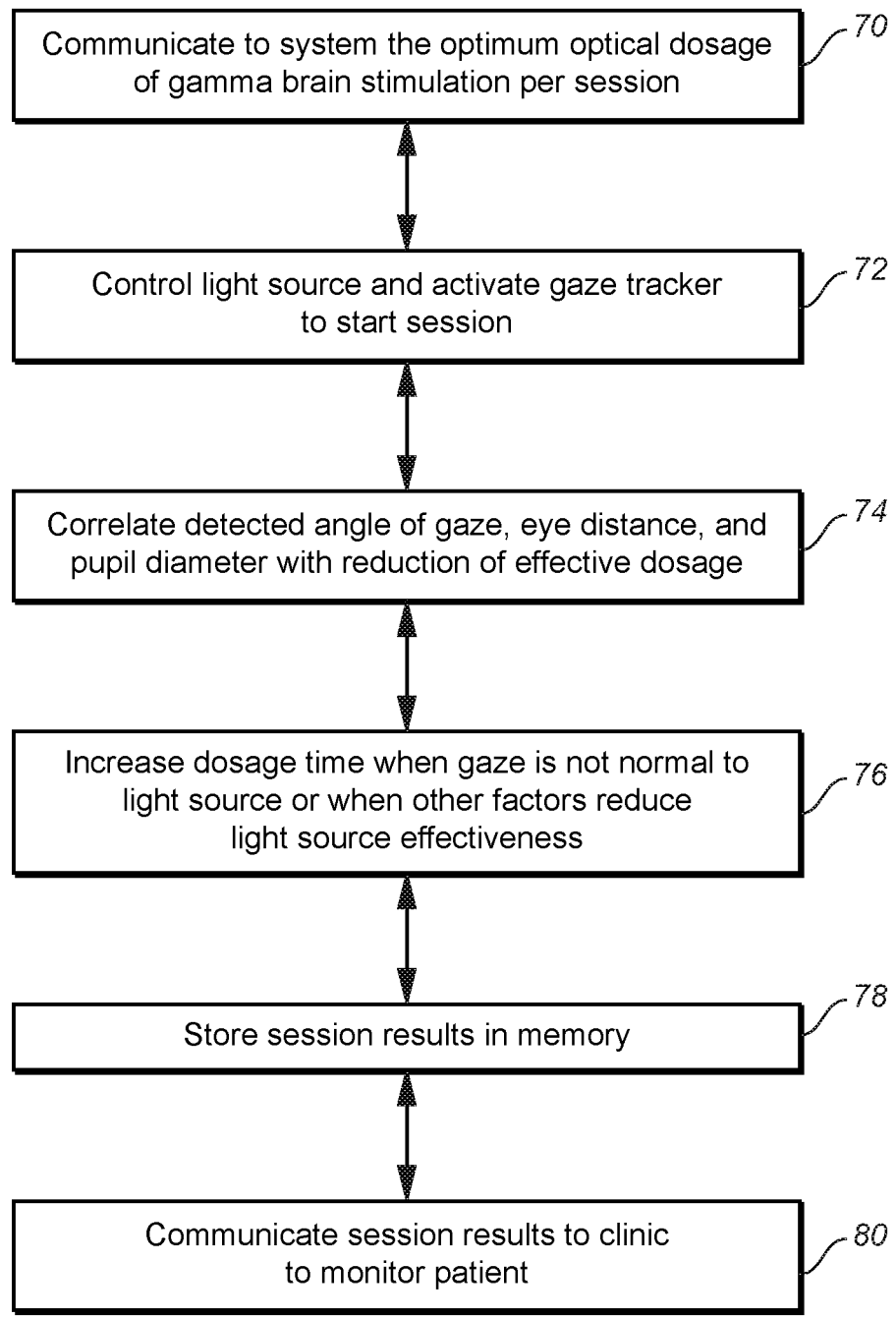
FIG. 5 is a flowchart identifying steps in a broad system process.

FIG. 5 is a broader flowchart summarizing certain steps in one method. In step 70, a medical worker or other source communicates to the system the optimal dosage of the gamma brain stimulation, which may be in the form of a session duration time using a known light source.

In step 72, the light source and gaze tracker are activated to start the session.

In step 74, the detected gaze angle, eye distance, and pupil diameter are correlated with a reduction of the effective dosage.

In step 76, the session time is extended, as required, to compensate for the detected gaze angle, eye distance, and pupil diameter. In another embodiment, the target dosage presumes some variation from ideal of the detected gaze angle, eye distance, and pupil diameter, and the system can add or subtract from the session time.

In step 78, the session data is stored in a memory for evaluating the efficacy of the treatment.

In step 80, a communications system conveys the data to a clinic or other medical worker. The communications system can also receive information, such as the target dose.

The system may be used for therapy or just to analyze the effects of the optical gamma brain stimulation on a group of similar persons for collecting further data for study. Other strobing frequencies besides 40 Hz may prove valuable with further studies.

The invention is not limited to a gamma brain stimulation rate of 20-140 Hz. Other frequency light pulses emitted by the light source 14 may be beneficial for beta brain waves (beta brain stimulation rate of 13-38 Hz) and circadian functions.

Definitions

The term "gamma brain stimulation" means a stimulus, such as a light source, that can change the neuronal gamma activity in the brain.

The term "person" means a subject to be subjected to gamma brain stimulation, such as a patient exhibiting symptoms of a brain disease such as Alzheimers, or such as a person who desires pre-emptive gamma brain stimulation, or a test-person who is subjected to gamma brain stimulation for instructive or test purposes.

The term "stimulation session" means a procedure over time where the person is exposed to a brain-stimulating device to receive a certain dosage of light. A single stimulation session is typically conducted within a day, but a customized session can be expanded and individualized to comprise multiple days, weeks, or months.

The term "stimulation duration" means a time period of a stimulation session, but is not limited to comprising the whole session duration, since the stimulation session time period can be broken up into multiple individual durations allowing for "interval" training, such as 15 minutes×4=60 minute session.

Strobing and flickering are used interchangeably in this application.

While particular embodiments of the present invention have been shown and described, it will be obvious to those skilled in the art that changes and modifications may be made without departing from this invention in its broader aspects and, therefore, the appended claims are to encompass within their scope all such changes and modifications that are within the true spirit and scope of this invention.

What is claimed is:

1. An optical gamma brain stimulation system for a person comprising:
    a processing system;
    a visible-wavelength light source configured to strobe at a brain stimulation rate between 13-140 Hz, the light source being remote from the person so as not to be supported by the person; and
    an eye-tracking device being remote from the person so as not to be supported by the person, the eye-tracking device being configured to detect an eye of the person and provide first data to the processing system as light from the light source is received into the eye of the person, the eye-tracking device comprising a camera and the processing system, wherein the eye-tracking device is configured to sense a gaze angle of the person with respect to the light source and an eye distance from the light source during a brain stimulation session, wherein the gaze angle and the eye distance are encoded in the first data,
    wherein the processing system is configured to detect a deviation in the gaze angle and the eye distance in real-time, correlate the deviation with a reduction of therapeutically effective light dosage, and automatically extend a duration of the brain stimulation session based on the first data and detected deviation as a dose correction measure to provide a pre-programmed therapeutically effective target light dosage to the person irrespective of the gaze angle and the eye distance with respect to the light source deviating from a designated gaze angle and eye distance required to deliver the therapeutically effective target light dosage to the person.

2. The stimulation system of claim 1, wherein the brain stimulation rate is between 20-140 Hz.

3. The stimulation system of claim 1, wherein the first data further encodes the person's pupil size.

4. The stimulation system of claim 1 further comprising a display of the duration of the brain stimulation session as the session duration is extended.

5. The stimulation system of claim 1 further comprising a memory, wherein second data corresponding to the brain stimulation session is stored in the memory for later retrieval.

6. The stimulation system of claim h wherein the brain stimulation system is used for treating effects of Alzheimer's disease, or preventing Alzheimer's disease, or treating a sleeping disorder.

7. The stimulation system of claim 1 further comprising a communications system, wherein the communications system transmits second data relating to the session for use in determining an efficacy of brain stimulation.

8. An optical gamma brain stimulation method for a person comprising:
    strobing a visible-wavelength light source at a brain stimulation rate between 13-140 Hz, the light source being remote from the person so as not to be supported by the person;
    detecting a gaze angle and an eye distance from the light source, using an eye-tracking device, to provide first data to a processing system as light from the light source is received into the person's eye, the eye-tracking device being remote from the person so as not to be supported by the person, the eye-tracking device comprising a camera and the processing system, wherein the eye-tracking device senses the sgaze angle with respect to the light source and the eye distance from the light source during a brain stimulation session, such that the gaze angle and the eye distance are encoded in the first data; and
    correlating, via the processing system, a deviation detected in real-time in the gaze angle and the eye distance with a reduction of therapeutically effective light dosage,
    automatically determining a dose correction measure by extending a duration of the brain stimulation session based on the first data and detected deviation; and
    causing the light source to provide a pre-programmed therapeutically effective target light dosage to the person irrespective of the detected gaze angle and the detected eye distance deviating from a designated gaze angle and eye distance required to deliver the therapeutically effective target light dosage to the person.

9. The stimulation method of claim 8, wherein the first data further encodes the person's pupil size.

10. The stimulation method of claim 8, wherein the brain stimulation method is used for treating effects of Alzheimer's disease, or preventing Alzheimer's disease, or treating a sleeping disorder.

\* \* \* \* \*